Jan. 30, 1940. C. SALBACH Plant Pat. 359
GLADIOLUS
Filed March 24, 1939
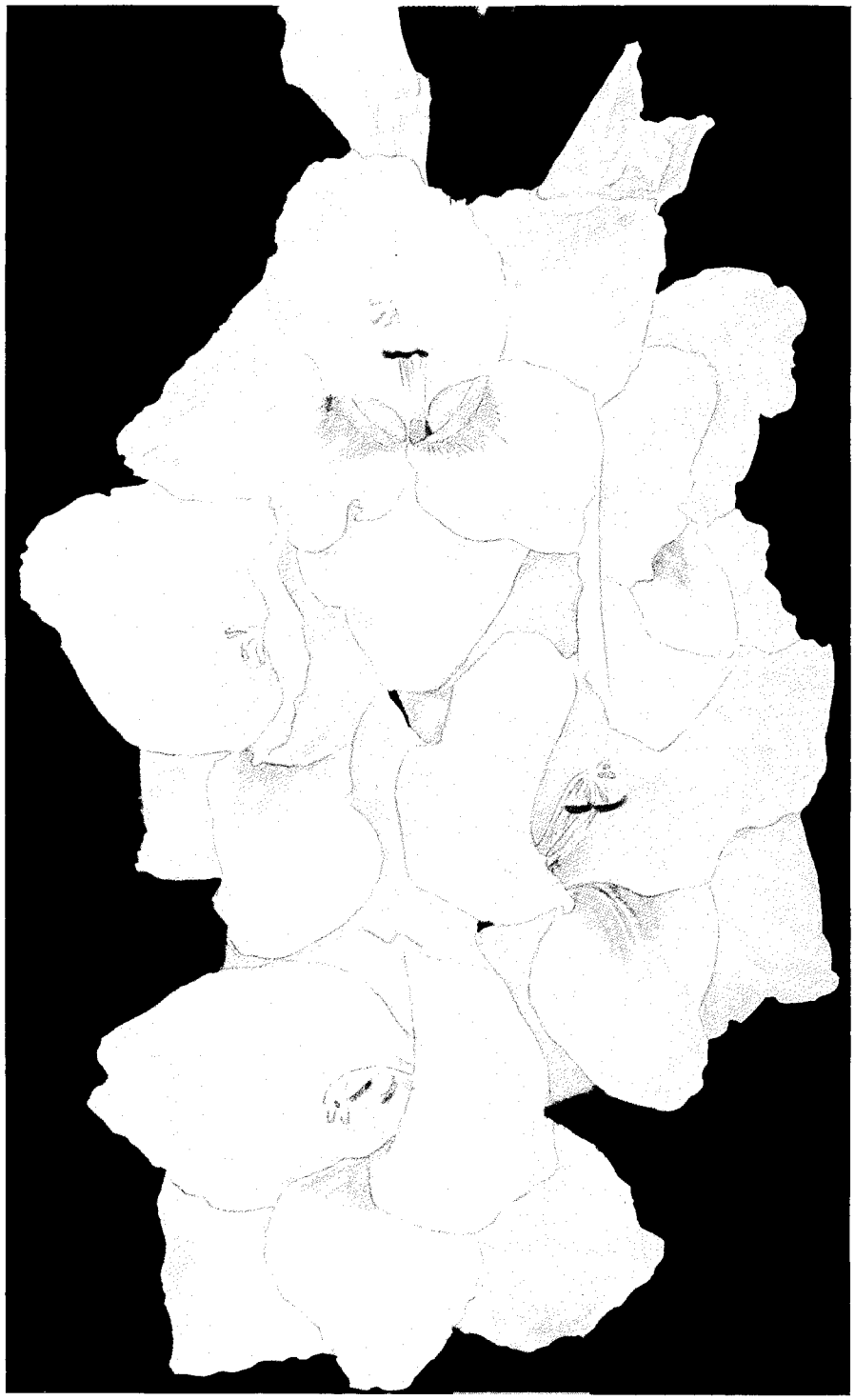
Inventor — Carl Salbach
By Orville M. Kile — Plant Patent Agent Patented Jan. 30, 1940

Plant Pat. 359

UNITED STATES PATENT OFFICE

359

GLADIOLUS

Carl Salbach, Contra Costa County, Calif., assignor to Ella S. Salbach, Contra Costa County, Calif.

Application March 24, 1939, Serial No. 264,001

1 Claim. (Cl. 47—60)

My present invention relates to improvements in flowering gladioli of superior Geranium to Eosine Pink with very large individual flowers of good quality which are unusually well placed and well formed.

My new gladiolus variety originated as a seedling produced from cross pollination work carried on by myself. The pollen parent was a seedling of my own, bred from Magna Blanca and an unnamed seedling, and the seed parent was the variety Picardy. This new variety was produced several years ago and has since been asexually reproduced by me, retaining its original qualities.

The illustration accompanying this specification shows a portion of a spike of this variety with flowers in approximately their true colors but somewhat reduced in size.

Color plate references are to Ridgway's Color Standards and Nomenclature.

Following is a more complete description of the plant and flower of this new variety of gladiolus.

*The plant*

Growth:

The plant is a very sturdy grower, the tip of spike usually being 42 inches above ground in my gardens. It is very consistent in producing fine spikes upon which the flowers are placed in symmetrical position, all facing in one direction.

Blooming:

Usually each spike opens five or six of its very large flowers at one time, and has a total of sixteen or seventeen flowers.

Foliage:

Usually seven leaves; Hay's Green (Plate XVIII); narrow; upright; about 12 inches long.

Stems:

Stiff and strong; fully adequate to hold the heavy flower spike in straight, upright position; two or more to each plant.

Corms:

High crowned; heavy; well covered.

*The flower*

The blossom:

*Size.*—The individual flowers are usually well over six inches in diameter, and some have reached eight inches in diameter. The flowers of this variety appear particularly large because they are so nearly round in form that they show a greater expanse of the face of each flower.

*Form.*—Nearly round. Consist of six petals of very uniform size and shape.

*Petals.*—Somewhat fluted, giving the flowers a slight ruffling. Substance—unusually heavy, making the variety very valuable for shipping and long keeping. Color—the colors in Ridgway's Color Standards which most nearly approach the colors of this new variety are; Geranium Pink (Plate I) fading lighter toward the center to Eosine Pink (Plate I), with a blotch on the throat petals that is slightly deeper, or approximately Begonia Rose (Plate I). The colors of this variety are very soft and rich.

*Stamens.*—The filaments of the three stamens are white. The anthers are white on top and Auricula Purple (Plate XXVI) beneath.

*Pistils.*—Medium size; Approximately La France Pink (Plate I). Young pistils extend considerably beyond stamens.

*Comparison*

Other varieties of somewhat similar coloring all have much smaller flowers. Frank J. McCoy, the closest approach to this new variety, has very much smaller flowers, is not as consistent in producing spikes whose blooms all face in the same direction, and its petal substance is not so firm. While the flowers of this variety are much larger than those of other varieties of similar coloring, there is an apparent difference in size greater than is shown by the measurements. This is because the blossom is nearly round in form and it gives a much greater expanse to the face of the flower than is true of other varieties.

The most notable characteristics which in combination readily distinguish my new gladiolus from all other known varieties of Geranium Pink to Eosine Pink, and particularly from Frank J. McCoy, are:

1. The very large size and round form of the flowers.
2. The vigorous and sturdy growth.
3. The heavy substance of the petals.
4. The consistency of producing flowers of good form and habit.
5. The soft, rich distinctive coloring.
6. The unusually good keeping and shipping qualities.
7. The general symmetry of the flowers and their ideal placement on the flower-head.

Having thus disclosed my invention, I claim:

The new variety of gladiolus plant herein described and illustrated, characterized particularly by its vigorous growth; its general symmetry; and its flowers of great size; round form; heavy substance; and soft, rich Geranium Pink coloring.

CARL SALBACH.